US00PP25526P3

(12) United States Plant Patent

Klemm et al.

(10) Patent No.: US PP25,526 P3

(45) Date of Patent: May 5, 2015

(54) *LOBELIA* PLANT NAMED 'KLELE12095'

(50) Latin Name: *Lobelia erinus*
Varietal Denomination: KLELE12095

(71) Applicant: Klemm+Sohn GmbH & Co. KG, Stuttgart (DE)

(72) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 163 days.

(21) Appl. No.: 13/986,951

(22) Filed: Jun. 18, 2013

(65) Prior Publication Data

US 2014/0373241 P1 Dec. 18, 2014

(51) Int. Cl.
*A01H 5/00* (2006.01)

(52) U.S. Cl.
USPC ..... Plt./451

(58) Field of Classification Search
USPC ..... Plt./451
See application file for complete search history.

(56) References Cited

PUBLICATIONS

PLUTO Plant Variety Database Jan. 14, 2015.*

* cited by examiner

*Primary Examiner* — Annette Para

(74) *Attorney, Agent, or Firm* — Barbara Campbell; James M. Weatherly; Cochran Freund & Young LLC

(57) ABSTRACT

A new *Lobelia* plant particularly distinguished by dark blue flowers, medium vigor, and medium earliness to flower, is disclosed.

1 Drawing Sheet

Genus and species: *Lobelia erinus*.
Variety denomination: 'KLELE12095'.

BACKGROUND OF THE NEW PLANT

The present invention comprises a new and distinct variety of *Lobelia*, botanically known as *Lobelia erinus*, and hereinafter referred to by the variety name 'KLELE12095'. 'KLELE12095' originated from a controlled cross conducted in September 2008 in Stuttgart, Germany between the female *Lobelia* 'KLELE06114' (U.S. Plant Pat. No. 19,680), also commercially known as MAGADI BASKET 'Dark Blue' having high vigor and later earliness, and the proprietary male *Lobelia* variety 'Z 052' (unpatented) having low vigor and dark violet flowers.

The seeds from the cross were sown and plants were grown in a greenhouse for evaluation, where an individual plant designated 'KLELE12095' was selected from the group of plants in May 2009. In May 2009, 'KLELE12095' was first vegetatively propagated by tissue culture and vegetative cuttings. 'KLELE12095' was found to reproduce true to type in successive generations of asexual propagation via tissue culture and vegetative cuttings.

CROSS REFERENCE TO RELATED APPLICATIONS

Plant Breeder's Rights for 'KLELE12095' were applied for in Canada on Feb. 8, 2013, Application No. 13-7919. 'KLELE12095' has not been made publicly available or sold more than one year prior to the filing date of this application.

SUMMARY

The following are the most outstanding and distinguishing characteristics of this new variety when grown under normal horticultural practices in Stuttgart, Germany.

1. Dark blue flowers; and
2. Medium vigor and medium earliness to flower.

DESCRIPTION OF THE PHOTOGRAPH

This new *Lobelia* plant is illustrated by the accompanying photograph which shows the plant's overall plant habit including form, foliage, and flowers. The photograph is of a four-month-old plant grown in a greenhouse in Stuttgart, Germany in May 2012. The colors shown are as true as can be reasonably obtained by conventional photographic procedures.

DESCRIPTION OF THE NEW VARIETY

The following detailed descriptions set forth the distinctive characteristics of 'KLELE12095'. The data which define these characteristics were collected from asexual reproductions carried out in Stuttgart, Germany. Data was collected on three-month-old plants grown in a greenhouse in Stuttgart, Germany in April 2013. Color references are to The R.H.S. Colour Chart of The Royal Horticultural Society of London (R.H.S.), 5$^{th}$ edition (2007).

Classification:

*Family.*—Campanulaceae.
*Botanical.*—*Lobelia erinus.*
*Common.*—*Lobelia.*
*Designation.*—'*KLELE*12095'.
*Parentage.*—Female parent: The *Lobelia* 'KLELE06114' (U.S. Plant Pat. No. 19,680), also commercially known as MAGADI BASKET 'Dark Blue'. Male parent: The proprietary *Lobelia* variety 'Z 052' (unpatented).

Growth:

*Growth and branching habit.*—Medium vigor, flat growing branches.

*Form.*—Rounded to flat.

*Height (measured from top of soil including flowers).*—7.0 cm.

*Width (horizontal plant diameter including any flowers).*—22.0 cm.

*Outdoor plant performance.*—Good.

*Time to produce a finished flowering plant.*—8 weeks.

*Time to initiate and develop roots.*—2 weeks.

*Root description.*—Fine, white.

Leaves:

*Arrangement.*—Alternate.

*Color, immature leaf.*—Upper surface: RHS 143A. Lower surface: RHS 138C.

*Color, mature leaf.*—Upper surface: RHS 137B. Lower surface: RHS 138C.

*Length.*—3.0 cm to 4.5 cm.

*Width.*—0.7 cm to 1.8 cm.

*Shape.*—Elliptic to lanceolate (upper leaves are more lanceolate).

*Apex.*—Obtuse.

*Base.*—Acute.

*Margin.*—Serrate (lanceolate leaves partly with entire margins).

*Texture (both upper and lower surfaces).*—Smooth.

*Venation type.*—Pinnate.

Stems:

*Length.*—12.0 cm to 15.0 cm.

*Diameter.*—0.2 cm.

*Internode length.*—0.5 cm to 2.0 cm.

*Color.*—RHS141B.

*Anthocyanin.*—Absent.

*Texture and appearance.*—Smooth.

*Peduncle.*—Length: 2.0 cm to 2.5 cm. Diameter: 0.05 cm. Texture: Smooth. Color: RHS 143A.

Flower buds:

*Shape.*—Inverse drop.

*Length.*—About 0.8 cm.

*Diameter.*—0.25 cm.

*Color (at tight bud).*—RHS 79A.

Inflorescence:

*Blooming habit.*—Continuous.

*Lastingness of individual blooms on the plant.*—About 1 week.

*Fragrance.*—Absent.

*Inflorescence type.*—Raceme.

*Quantity of flowers and buds per flowering branch.*—6 to 10.

Flowers:

*Flower diameter.*—2.0 cm.

*Flower height.*—0.4 cm.

*Mature flower.*—Upper lobe: Color, upper surface: RHS N89A. Color, lower surface: RHS N89D. Length: 0.7 cm. Width: 0.1 cm. Shape: Lanceolate. Apex: Acute. Margin: Entire. Texture, both upper and lower surfaces: Smooth. Lower lobes: Color, upper surface: RHS N89A. Color, lower surface: RHS 97D towards the bottom, RHS 96B towards the tip. Length: 1.0 cm. Width: 0.7 cm. Shape: Obovate. Apex: Obtuse. Margin: Entire. Texture, both upper and lower surfaces: Smooth. Corolla tube: Color inside: RHS NN155D (White) with RHS 90A blue pattern. Color outside: RHS 92C. Tube length: 0.3 cm. Diameter: 0.2 cm. Calyx: Length: 0.3 cm fused part and 0.8 cm for non-fused part. Diameter: 0.1 cm. Shape: Funnel, star-shaped (sepals are fused in lower half). Apex: Acute. Texture: Smooth. Color: RHS 137B.

Reproductive organs:

*Stamens.*—Quantity per flower: 5. Filament length: 0.5 cm. Filament color: RHS 96C. Anther length: 0.2 cm. Anther width: 0.1 cm. Anther color: RHS N77C. Pollen amount: Moderate. Pollen color: Greyed-yellow.

*Pistils.*—Quantity per flower: 1. Pistil length: 0.7 cm. Stigma shape: Rounded, two-sided. Stigma color (mature): RHS N92A (Greyed-violet). Style length: 0.6 cm. Style color: RHS 142C. Ovary color: RHS 142B.

Fruit and seed set: Fruit and seed set observed later in the year.

Disease and pest/insect resistance: No disease and pest/insect resistance observed.

COMPARISON WITH PARENTAL LINES AND KNOWN VARIETY

'KLELE12095' is a distinct variety of *Lobelia* having medium vigor, medium earliness to flower and dark blue flowers. 'KLELE12095' is distinguished from its parents, the female parent 'KLELE06114' (U.S. Plant Pat. No. 19,680), also commercially known as MAGADI BASKET 'Dark Blue' and the male parent, 'Z 052' (unpatented), as described in Table 1.

TABLE 1

Comparison with Parental Lines

| Characteristic | 'KLELE12095' | Female Parent 'KLELE06114' | Male Parent 'Z 052' |
|---|---|---|---|
| Vigor | Medium | Moderate | Low |
| Earliness | Medium early | Late | |
| Flower color | Dark blue | | Dark violet |

'KLELE12095' is most similar to the commercial *Lobelia 'KLELE*06114' (U.S. Plant Pat. No. 19,680), also commercially known as MAGADI BASKET 'Dark Blue'. Differences between the varieties are described in Table 2.

TABLE 2

Comparison with Similar Variety

| Characteristic | 'KLELE12095' | 'KLELE06114' |
|---|---|---|
| Vigor | Medium | Moderate |
| Earliness | Medium early | Late |

We claim:

1. A new and distinct variety of *Lobelia* plant designated 'KLELE12095' as shown and described herein.

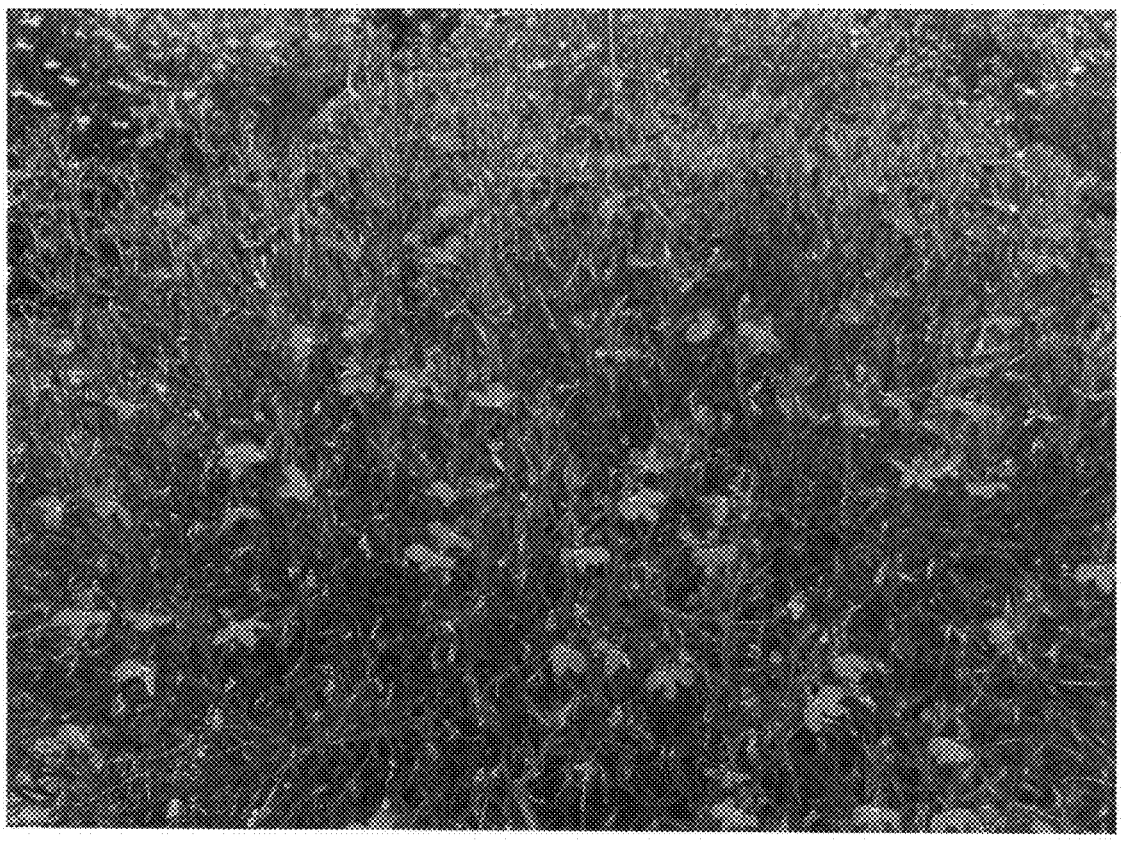

* * * * *